US012678432B2

(12) United States Patent
Tang et al.

(10) Patent No.: US 12,678,432 B2
(45) **Date of Patent: *Jul. 14, 2026**

(54) SUBSTITUTED CROTONAMIDE PHARMACEUTICAL COMPOSITION AND PREPARATION METHOD THEREFOR

(71) Applicant: Jiangsu Medolution LTD, Taizhou (CN)

(72) Inventors: Haitao Tang, Nanjing (CN); Bei Wang, Nanjing (CN); Bin Ge, Nanjing (CN); Haitao Ge, Nanjing (CN); Zhengjun Wang, Nanjing (CN)

(73) Assignee: Jiangsu Medolution Ltd, Taizhou (CN)

( * ) Notice: Subject to any disclaimer, the term of this patent is extended or adjusted under 35 U.S.C. 154(b) by 1037 days.

This patent is subject to a terminal disclaimer.

(21) Appl. No.: 17/780,512

(22) PCT Filed: Nov. 26, 2020

(86) PCT No.: PCT/CN2020/131636

§ 371 (c)(1),
(2) Date: May 26, 2022

(87) PCT Pub. No.: WO2021/104340

PCT Pub. Date: Jun. 3, 2021

(65) Prior Publication Data

US 2023/0000855 A1 Jan. 5, 2023

(30) Foreign Application Priority Data

Nov. 27, 2019 (CN) ........................ 201911180660.1

(51) Int. Cl.
*A61K 31/4709* (2006.01)
*A61K 9/48* (2006.01)
*A61K 31/4706* (2006.01)

(52) U.S. Cl.
CPC .......... *A61K 31/4709* (2013.01); *A61K 9/485* (2013.01); *A61K 9/4858* (2013.01); *A61K 9/4866* (2013.01); *A61K 31/4706* (2013.01)

(58) Field of Classification Search
CPC .. A61K 31/4709; A61K 9/485; A61K 9/4858; A61K 9/4866; A61K 31/4706
See application file for complete search history.

(56) References Cited

U.S. PATENT DOCUMENTS 8,748,453 B2 * 6/2014 Zhang ................. C07D 215/56 546/152

* cited by examiner

*Primary Examiner* — Robert A Wax
*Assistant Examiner* — Olga V. Tcherkasskaya

(57) ABSTRACT

A composition of substituted crotonamide pharmaceutical and a preparation method therefor. The pharmaceutical composition comprises 5-50 parts of (E)-N-(3-cyano-7-ethoxy-4-(3-ethynylphenylamino)quinolin-6-yl)-4-(dimethylamino)but-2-enamide maleate, 40-120 parts of a filler, 2-20 parts of a disintegrant, 0-6 parts of an adhesive, and 0.5-5 parts of a lubricant. The filler is selected from carbohydrates.

18 Claims, No Drawings

SUBSTITUTED CROTONAMIDE PHARMACEUTICAL COMPOSITION AND PREPARATION METHOD THEREFOR

CROSS-REFERENCE

This application is a 371 U.S. National Phase Filing of International Patent Application No. PCT/CN2020/131636, filed Nov. 26, 2020, which claims the benefit of Chinese Patent Application No. 201911180660.1, filed Nov. 27, 2019, each of which applications is entirely incorporated herein by reference.

FIELD OF THE INVENTION

The present invention is directed to pharmaceutical formulations, specifically related to pharmaceutical formulations of substituted crotonamide, the preparation thereof, and the use of such formulations to treat kinase mediated diseases and conditions such as cancer.

BACKGROUND OF THE INVENTION

Lung cancer is a malignant tumor with the highest morbidity and mortality in the world. Non-small cell lung cancer (NSCLC) represents approximately 80% of all lung cancers. Adenocarcinoma is the highest incidence of non-small cell lung cancer. Currently, adenocarcinoma has been found to drive gene mutations, including EGFR, ALK, and ROS1 mutations. The use of targeted drugs for mutated genes has significantly improved the survival time of patients compared to the use of old chemotherapy drugs. Targeted drugs for the treatment of non-small cell lung cancer with gene mutations have an effective rate of more than 70%, and twice the time on average to place the tumors under control than that of chemotherapy, with fewer side effects and higher quality of life for patients.

The epidermal growth factor receptor (EGFR) tyrosine kinase inhibitors (TKIs) are an effective therapy on patients with EGFR mutation-positive NSCLC. EGFR-TKI is the first-line treatment of NSCLC. EGFR-TKIs used include first-generation drugs of gefitinib, erlotinib, and icotinib, second-generation drugs of dacomitinib and afatinib, and third-generation drug osimertinib. By blocking the activation signals of EGFR tyrosine kinase phosphorylation and the downstream MAPK and AKT signal pathways in cancer cells, EGFR-TKIs can inhibit tumor proliferation, promote tumor cell apoptosis, and inhibit tumor angiogenesis, whereby inhibiting tumor growth.

SUMMARY OF THE INVENTION

Substituted butenamide compound (E)-N-(3-cyano-7-ethoxy-4-(3-ethynylphenylamino)quinolin-6-yl)-4-(dimethylamino)but-2-enamide, or salt thereof is EGFR-TKIs, suitable for non-small cell lung cancer, (E)-N-(3-cyano-7-ethoxy-4-(3-ethynylphenylamino)quinolin-6-yl)-4-(dimethylamino)but-2-enamide maleate salt, also known as (E)-N-{4-[(3-ethynylphenylamino)-3-cyano-7-ethoxy-6-quinolinyl]}-4-(dimethylamino)-2-butenamide maleate salt. Its structural formula is shown in the following Formula (I):

Formula (I)

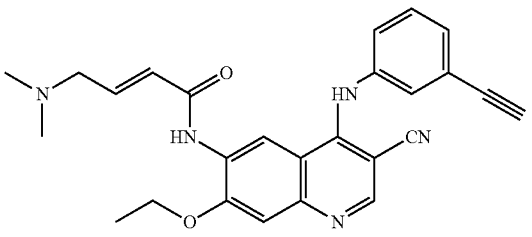

(E)-N-(3-cyano-7-ethoxy-4-(3-ethynylphenylamino)quinolin-6-yl)-4-(dimethylamino)but-2-enamide or its salt is sensitive to damp heat. Under the conditions of damp heat, an impurity A as shown in Formula (II) is generated.

Formula (II)

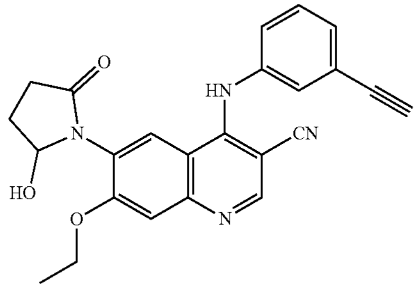

There is no prior art literature of controlling or inhibiting the production of impurity A (Formula (II)) using known techniques or formulation compositions from Formula (I).

The technical problem to be solved by the present invention is to provide a pharmaceutical composition of the substituted crotonamide compound (E)-N-(3-cyano-7-ethoxy-4-(3-ethynylphenylamino)quinolin-6-yl)-4-(dimethylamino)but-2-enamide (Formula (I)) or its salts. The pharmaceutical composition exhibits good stability.

In one aspect of the present invention, there is provided a pharmaceutical composition of (E)-N-(3-cyano-7-ethoxy-4-(3-ethynylphenylamino) quinolin-6-yl)-4-(dimethylamino) but-2-enamide, or salt thereof, comprising: from 5 parts to 50 parts of (E)-N-(3-cyano-7-ethoxy-4-(3-ethynylphenylamino) quinolin-6-yl)-4-(dimethylamino) but-2-enamide or salt thereof, from 40 parts to 120 parts of filler, from 2 parts to 20 parts of disintegrant, from 0 to 6 parts of binder, and from 0.5 part to 5 parts of lubricant, in parts by weight of the components.

In some embodiments, the pharmaceutical composition comprises: from 8 parts to 12 parts of (E)-N-(3-cyano-7-ethoxy-4-(3-ethynylphenylamino) quinolin-6-yl)-4-(dimethylamino) but-2-enamide or salt thereof, from 50 parts to 100 parts of filler, from 4 parts to 15 parts of disintegrant-4-15 parts, from 0.3 to 5 parts of binder-0.3-5 parts, and from 0.5 to 5 parts of lubricant, in parts by weight of the components. In some embodiments, the pharmaceutical composition comprises: from 9 parts to 11 parts of (E)-N-(3-cyano-7-ethoxy-4-(3-ethynylphenylamino) quinolin-6-yl)-4-(dimethylamino) but-2-enamide or salt thereof, from 65 parts to 90 parts of filler, from 5 parts to 12 parts of disintegrant, from 0.5 to 3 parts of binder, and from 0.5 to 4 parts of lubricant, in parts by weight of the components. In some embodiments, the pharmaceutical composition comprises: 10 parts of (E)-N-(3-cyano-7-ethoxy-4-(3-ethynylphenylamino)quinolin-6-yl)-4-(dimethylamino) but-2-enamide or salt thereof-10 parts, from 65 parts to 90 parts of filler, from 5 parts to 12 parts of disintegrant, from 0.5 to 3 parts of binder, and from 0.5 to 4 parts of lubricant, in parts by weight of the components.

The filler is carbohydrates, preferably sugar compounds, more preferably sugar alcohols. The sugar alcohol is one or more of mannitol, xylitol, sorbitol, or lactose, and more preferably one or more of mannitol and lactose.

The disintegrant is one or more of sodium carboxymethyl starch or sodium croscarmellose, preferably sodium carboxymethyl starch.

The binder is one or more of hydroxypropyl cellulose or hypromellose, preferably hydroxypropyl cellulose.

The lubricant is one or more of glyceryl behenate, sodium stearyl fumarate, ord talc, preferably glyceryl behenate.

The aforementioned salt of (E)-N-(3-cyano-7-ethoxy-4-(3-ethynylphenylamino)quinolin-6-yl)-4-(dimethylamino) but-2-enamide is pharmaceutically acceptable salt.

The pharmaceutically acceptable salts include salts that are commonly used to form alkali metal salts or form salts by adding free acids or free bases approved by the regulatory agencies. Salts are formed through ionic association, charge-charge interaction, covalent bonding, complexation, coordination, etc. The salt is pharmaceutically acceptable.

The types of the pharmaceutically acceptable salts include, but are not limited to, acid addition salts formed by reacting the free base form of the compound with the following pharmaceutically acceptable acids: inorganic acids, such as hydrochloric acid, hydrobromic acid, sulfuric acid, phosphoric acid, etc.; or organic acids, such as acetic acid, propionic acid, glycolic acid, pyruvic acid, lactic acid, malonic acid, succinic acid, malic acid, maleic acid, fumaric acid, tartaric acid, citric acid, methanesulfonic acid, benzenesulfonic acid, toluenesulfonic acid, gluconic acid, glutamic acid, hydroxynaphthoic acid, or salicylic acid, etc.

Other examples of such salts can be found in Berge et al., J. Pharm. Sci, 66, 1 (1977). In some embodiments, conventional methods are used to form the salt. For example, the compound of the present invention is prepared by mixing the free base of the desired compound in the desired solvent or combination of solvents with the desired stoichiometric amount of phosphoric acid at a desired temperature, usually under heating (depending on the boiling point of the solvent), thereby forming the desired phosphate salt. In one embodiment, the salt precipitates and crystallizes (i.e., if it has crystalline properties) after cooling (slowly or rapidly). In addition, this application also includes hemi-salt, mono-salt, di-salt, tri-salt, and multiple-salt forms of the claimed compounds of the present invention. Similarly, this application also includes the claimed compound, or its salt or hemihydrate, monohydrate, dihydrate, trihydrate, and polyhydrate forms.

In some embodiments, the compound is hydrochloride, hydrobromide, sulfate, phosphate or metaphosphate, acetate, propionate, caproate, cyclopentane propionate, glycolic acid Salt, pyruvate, lactate, malonate, succinate, malate, maleate, fumarate, trifluoroacetate, tartrate, citrate, benzoate, 3-(4-hydroxybenzoyl)benzoate, cinnamate, mandelate, methanesulfonate, ethanesulfonate, 1,2-ethanedisulfonate, 2-hydroxyethanesulfonic acid salt, benzenesulfonate, toluenesulfonate, 2-naphthalenesulfonate, 4-methylbicyclo-[2.2.2]oct-2-ene-1-carboxylate, glucoheptonate, 4'4-methylene-bis-(3-hydroxy-2-ene-1-carboxylic acid) salt, 3-phenylpropionate, trimethyl acetate, tert-butyl acetate, lauryl sulfate, gluconate, glutamate, naphthoate, salicylate, stearate, muconate, butyrate, phenylacetate, phenylbutyrate, valproate acid salts and so on.

In a preferred embodiment, the salt of the compound is hydrochloride, benzenesulfonate, methanesulfonate, maleate, or a hydrate thereof, such as a monohydrate. Specifically, (E)-N-(3-cyano-7-ethoxy-4-(3-ethynylphenylamino)quinolin-6-yl)-4-(dimethylamino)but-2-enamide maleate and its monohydrate are particularly suitable.

The water content in the pharmaceutical composition of the present invention is preferably 5 wt % or less by the total weight of the formulation, more preferably 3 wt % or less, even more preferably 2 wt % or less, or 1.5 wt % or less, and 1 wt % or less by the total weight of the formulation is also particularly suitable.

The pharmaceutical composition of the present invention further includes pharmaceutically acceptable excipients, including but not limited to, carriers, excipients, binders, fillers, suspending agents, fragrances, sweeteners, and disintegrants, dispersant, surfactant, lubricant, colorant, diluent, solubilizer, wetting agent, plasticizer, stabilizer, penetration enhancer, wetting agent, defoamer, antioxidant, preservative, or a combination thereof. The pharmaceutical composition facilitates the administration of the compound to an organism.

The pharmaceutical composition of the present invention can be further made into pharmaceutical preparations to facilitate administration to patients. The pharmaceutical preparations include, but are not limited to, aqueous liquid dispersions, self-emulsifying dispersions, solid solutions, liposome dispersions, and aerosols. Agents, solid dosage forms, powders, immediate release formulations, controlled release formulations, fastmelt formulations, tablets, capsules, pills, delayed release formulations, extended release formulations, pulse release formulations, multiparticulate formulations, and mixed immediate release formulations, and controlled release formulations.

Another aspect of the present invention provides the method of preparing the pharmaceutical compositions comprising (E)-N-(3-cyano-7-ethoxy-4-(3-ethynylphenylamino)quinolin-6-yl)-4-(dimethylamino)but-2-enamide, or salt thereof. The preparation method includes the following steps:

(1) Premix: Adding (E)-N-(3-cyano-7-ethoxy-4-(3-ethynylphenylamino)quinolin-6-yl)-4-(dimethylamino)but-2-enamide or its salt, filler and disintegrant. Then mixing them uniformly;

(2) Wet granulation: adding a binder solution to soften the materials, sieving and granulating the mixture to obtain wet granules;

(3) Drying, granulation and total mixing: the wet granules are dried and then sieved and granulated, and a lubricant is added for complete mixing the ingredients to prepare the pharmaceutical composition. The pharmaceutical composition can be further compressed into tablets, or capsules, and the compostions can be filled into capsules. Wherein, the pre-mixing method in step (1) includes jet pulverization pre-mixing, sieving pre-mixing, and wet granulator pre-mixing; and the binder in step (2) is prepared with purified water, and its concentration is 2-10% by weight. The wet granulation in step (2) can be carried out using a wet granulator or a fluidized bed, preferably a fluidized bed granulation drying; the drying in step (3) can be carried out by blast drying or a fluidized bed, preferably a fluidized bed fluidized bed; the moisture of the particles after drying is controlled within 1.5 wt %, preferably within 1 wt %.

The present invention provides another method for the preparation pharmaceutical compositions of (E)-N-(3-cyano-7-ethoxy-4-(3-ethynylphenylamino)quinolin-6-yl)-4-(dimethylamino)but-2-enamide or its salt. The preparation method includes the following steps:

(1) Pre-mixing: Mix the active ingredients, fillers, and disintegrants uniformly;

(2) Drying and total mixing: After drying, the powder is mixed with lubricant. The pre-mixing method in step (1) includes jet pulverization and pre-mixing, sieving and pre-mixing, and wet granulator pre-mixing; in step (2), the drying can be carried out by blast drying, and the moisture content after drying is controlled at 3 wt % or within 1.5% by weight, preferably within 1% by weight.

Specifically, in the preparation process of the pharmaceutical composition of the present invention, (E)-N-(3-cyano-7-ethoxy-4-(3-ethynylphenylamino)quinolin-6-yl)-4-(dimethylamino)but-2-enamide or its salt is mixed with filler and disintegrant uniformly, then the binder solution is added to prepare soft material, then granulated and dried; controlling the moisture of the granules after drying to be within 3% or 1.5%, and finally adding a lubricant to make the pharmaceutical composition. The pharmaceutical composition can be added with other pharmaceutically acceptable excipients to make pharmaceutical preparations such as tablets or capsules. Or mixing the active ingredient (E)-N-(3-cyano-7-ethoxy-4-(3-ethynylphenylamino)quinolin-6-yl)-4-(dimethylamino)but-2-enamide or its salt uniformly with fillers and disintegrants, then the lubricant is added to the total mix, dried, and the moisture content after drying is controlled to be within 3 wt % or 1.5 wt % to prepare the pharmaceutical composition. The pharmaceutical composition can be made into pharmaceutical preparations such as tablets or capsules by adding other pharmaceutically acceptable auxiliary materials.

More specifically, the preferred preparation method of the pharmaceutical composition of the present invention includes the following steps:

(1) Pre-mixing: Mix the active ingredients, fillers, and disintegrants uniformly;

(2) Wet granulation: adding binder solution to soften the material, and granulating with 20-30 mesh sieve;

(3) Drying, granulation and total mixing: the wet granules are dried and then passed through a 0-30 mesh sieve to be granulated, and lubricants are added for total mixing to prepare the pharmaceutical composition.

The detection of impurity A in the present invention is described as follows:

Instrument: Agilent 1260 High Performance Liquid Chromatography, Column: Agilent ZORBAX Extend (4.6 mm×250 mm, 5 μm), mobile phase: 1 wt % ammonium acetate aqueous solution (pH adjusted to 7.0 with triethylamine or acetic acid) as mobile phase A, acetonitrile is the mobile phase B; the gradient elution procedure is shown in Table 1. Detection wavelength: 261 nm, flow rate: 1.0 mL/min, column temperature: 25° C., injection volume: 10 μL, solution preparation: diluent:acetonitrile-water (v/v 60:40).

TABLE 1

| Mobile phase gradient elution parameters | | |
|---|---|---|
| Time (min) | Mobile phase A (%) | Mobile Phase B (5) |
| 0 | 39 | 61 |
| 25 | 39 | 61 |

TABLE 1-continued

| Mobile phase gradient elution parameters | | |
|---|---|---|
| Time (min) | Mobile phase A (%) | Mobile Phase B (5) |
| 50 | 70 | 30 |
| 50.01 | 39 | 61 |
| 60 | Stop | |

The advantage of the present invention are:

The use of the pharmaceutical composition of the present invention greatly improves the fluidity of the material, and solves the problems of difficulties caused by the high viscosity of the raw material during the preparation process such that the mixture is easily adhere to the container wall, thereby producing lower content or yield for the finished product, and increased amount of impurity A. In addition, the new formulation has high quality and stability.

DETAILED EXAMPLES

The following examples present some details disclosure of (E)-N-(3-cyano-7-ethoxy-4-(3-ethynylphenylamino)quinolin-6-yl)-4-(dimethylamino)but-2-enamide maleate monohydrate (hereinafter referred to as "active pharmaceutical ingredient" or "API") and the preparation method for the pharmaceutical compositions of the API. But these examples do not limit the present invention in any possible ways. The API is prepared according to the method described in CN104513200A, the content of which is incorporated in its entirety.

Example 1

The single-dose prescription composition is shown in Table 2.

TABLE 2

| Ingredient | Single dose (mg) |
|---|---|
| API | 20 |
| Mannitol | 120 |
| Microcrystalline cellulose | 35 |
| Crospovidone | 7 |
| Povidone K30 | 5 |
| Magnesium stearate | 1 |
| Colloidal silica | 5 |
| Total | 193 |

Add the previously determined amount of API, mannitol, microcrystalline cellulose, and cross-linked povidone into a wet granulator, mix well and prepare a softened material with 15 wt % povidone K30 as a binder, and pass through a 20-mesh sieve to form granules. Dry and control the particle moisture within 1.5 wt %. After granulated by 10 mesh, the granules are added with the previously determined amount of magnesium stearate and colloidal silicon dioxide, and the intermediate granules are mixed for capsule filling.

Example 2

The single-dose prescription composition is shown in Table 3.

TABLE 3

| Ingredient | Single dose (mg) |
|---|---|
| API | 20 |
| Microcrystalline cellulose | 170 |
| Povidone K30 | 10 |
| Glyceryl behenate | 4 |
| Colloidal silica | 2 |
| Total | 206 |

Add the pre-determined amount of API and microcrystalline cellulose into the wet granulator, mix well, and prepare a softened material with 15 wt % povidone K30 as the binder, pass through a 20-mesh sieve, granulate and dry, and control the particle moisture to within 1.5 wt %. After passing 0-30 mesh size, the granules are added with the pre-determined amount of glyceryl behenate and colloidal silicon dioxide, and the intermediate granules are mixed for capsule filling.

Example 3

The single-dose prescription composition is shown in Table 4.

TABLE 4

| Ingredient | Single dose (mg) |
|---|---|
| API | 20 |
| Microcrystalline cellulose | 170 |
| Povidone K30 | 10 |
| Glyceryl behenate | 4 |
| Colloidal silica | 2 |
| Total | 206 |

Add the pre-determined amount of API and mannitol into a wet granulator, mix well, and prepare a softened material with 15 wt % povidone K30 as a binder, pass through a 20-mesh sieve to granulate, and dry. Control the water content of the granules to within 1.5 wt %. After sizing, the granules are added with the pre-determined amount of glyceryl behenate and colloidal silicon dioxide, and the intermediate granules are filled in capsules after total mixing.

Example 4

Single-dose prescription composition, see Table 5.

TABLE 5

| Ingredient | Single dose (mg) |
|---|---|
| API | 20 |
| Mannitol | 160 |
| Sodium Carboxymethyl Starch | 10 |
| Hydroxypropyl cellulose | 1 |
| Glyceryl behenate | 4 |
| Total | 195 |

Add the pre-determined amount of API, mannitol, and sodium carboxymethyl starch into a wet granulator, mix well, and prepare a softened material with 4 wt % hydroxypropyl cellulose as a binder, pass through a 20-mesh sieve to granulate, dry, and control the granulation. The moisture content is controlled to be within 1.5 wt %. After granulated with 10 mesh, the granules are added with the pre-determined amount of glyceryl behenate, and the intermediate granules are mixed for capsule filling.

The capsule granules of Examples 1, 2, 3, and 4 were placed in an open weighing bottle and placed at a high temperature of 40° C. for 1 month. After being taken out, the content (%) of related substances was measured. The results are shown in Table 6.

TABLE 6

| time | Example 1 | Example 2 | Example 3 | Example 4 |
|---|---|---|---|---|
| 0 days | 0.08 | 0.07 | 0.05 | 0.04 |
| 14 days | 0.15 | 0.32 | 0.12 | 0.08 |
| 1 month | 0.24 | 0.46 | 0.26 | 0.14 |

The above results indicate that the impurity A of the composition of Example 4 increases slowly after being placed for 1 month under high temperature conditions. It shows that the pharmaceutical composition prepared according to the technical aspects of the present invention is significantly more stable than previously prepared/reported compositions.

Example 5

The single-dose prescription composition is shown in Table 7.

TABLE 7

| Ingredient | Single dose (mg) |
|---|---|
| API | 20 |
| Mannitol | 200 |
| Sodium Carboxymethyl Starch | 10 |
| Hydroxypropyl cellulose | 3 |
| Glyceryl behenate | 5 |
| Total | 238 |

Add the prescription amount of active ingredients, mannitol and sodium starch glycolate into the wet granulator, mix well and prepare a softened material with 4% hydroxypropyl cellulose as the binder, pass through a 20-mesh sieve, granulate, dry, and prepare Moisture 0.8 wt %, 1.0 wt %, 1.4 wt % particles. After sizing, each granule is added with a prescription amount of glyceryl behenate, and the intermediate granules are encapsulated after total mixing.

The capsule particles containing different moisture of Example 5 were placed for 14 days under the conditions of high temperature 40° C., high humidity 92.5% RH, light 4500 lux, and accelerated (high temperature 40° C., high humidity 75%), and then the related substances were measured after being taken out. The content (%) of impurity A is shown in Table 8.

TABLE 8

| Relative substance (%) | 0.8% moisture particles | 1.0% moisture particles | 1.4% moisture particles |
|---|---|---|---|
| 0 days | 0.03 | 0.03 | 0.04 |
| High temperature 14 days | 0.09 | 0.10 | 0.10 |

TABLE 8-continued

| Relative substance (%) | 0.8% moisture particles | 1.0% moisture particles | 1.4% moisture particles |
|---|---|---|---|
| High humidity for 14 days | 0.08 | 0.07 | 0.08 |
| 14 days of light | 0.07 | 0.08 | 0.08 |
| 14 days accelerated | 0.09 | 0.08 | 0.09 |

The above results indicate that the formulation composition with the particle moisture within 1.5 wt % is relatively stable.

Example 6

Single-dose prescription composition, see Table 9.

TABLE 9

| Ingredient | Single dose (mg) |
|---|---|
| API | 20 |
| Mannitol | 160 |
| Crospovidone | 10 |
| Hydroxypropyl cellulose | 1 |
| Glyceryl behenate | 4 |
| Total | 195 |

Add the prescription amount of active ingredients, mannitol, and cross-linked povidone into a wet granulator, mix well and prepare a softened material with 4 wt % hydroxypropyl cellulose as a binder, pass through a 20-mesh sieve to granulate, and dry. Control the moisture of the granules to be within 1.5 wt %. After sizing, the granules are added with the prescription amount of glyceryl behenate, and the intermediate granules are filled in the capsule after the total mixing.

Example 7

Single-dose prescription composition, see Table 10.

TABLE 10

| ingredient | Single dose (mg) |
|---|---|
| API | 20 |
| Mannitol | 130 |
| Sodium starch glycolate | 20 |
| Hydroxypropyl cellulose | 1 |
| Glyceryl behenate | 1 |
| Total | 172 |

Add the active ingredients, mannitol, and sodium starch glycolate into the wet granulator and mix well, prepare the softened material with 4 wt % hydroxypropyl cellulose as the binder, pass through a 20-mesh sieve to granulate and dry, and control the water content of the granules to be within 1.5 wt %. The pre-determined amount of glyceryl behenate is added, and the intermediate is mixed for capsule filling.

Example 8

Single-dose prescription composition, see Table 11.

TABLE 11

| ingredient | Single dose (mg) |
|---|---|
| API | 20 |
| Lactose monohydrate | 160 |
| Sodium starch glycolate | 10 |
| Hydroxypropyl cellulose | 1.5 |
| Glyceryl behenate | 8 |
| Total | 199.5 |

Add the pre-determined amount of active ingredients, lactose monohydrate and sodium starch glycolate into the wet granulator, mix well and prepare the softened material with 4% hydroxypropyl cellulose as the binder, pass through a 20-mesh sieve to granulate and dry to control the moisture of the granules to be within 1.5%. After sizing, the granules are added with the pre-determined amount of glyceryl behenate, and the intermediate granules are filled in the capsule after the total mixing.

The capsules of Examples 1, 2, 3, 4, 6, 7, and 8 were packaged in high-density polyethylene bottles, 20 capsules/bottle, and 2 bags/bottle of desiccant were added to an accelerated conditions (high temperature 40° C., high humidity 75%) and placed under the accelerated conditions for 3 months. The content (%) change results of impurity A in each batch are shown in Table 12.

TABLE 12

| Impurity A (%) | Example 1 | Example 4 | Example 6 | Example 7 | Example 8 |
|---|---|---|---|---|---|
| 0 days | 0.08 | 0.04 | 0.09 | 0.05 | 0.06 |
| After 1 month | 0.28 | 0.14 | 0.15 | 0.15 | 0.12 |
| After 2 month | 0.48 | 0.20 | 0.25 | 0.21 | 0.18 |
| After 3 month | 0.62 | 0.20 | 0.47 | 0.22 | 0.20 |

The above results show that the stability of the formulations of Examples 4, 7, and 8 is significantly higher than the other formulations after being placed for 3 months under accelerated conditions, indicating that the stability of the capsule prepared according to the technical designs of the present invention is significantly improved.

What is claimed is:

1. A pharmaceutical composition comprising (E)-N-(3-cyano-7-ethoxy-4-(3-ethynylphenylamino)quinolin-6-yl)-4-(dimethylamino)but-2-enamide maleate or hydrate thereof, wherein the pharmaceutical composition comprises: 5-50 mg of (E)-N-(3-cyano-7-ethoxy-4-(3-ethynylphenylamino)quinolin-6-yl)-4-(dimethylamino)but-2-enamide maleate or hydrate thereof, 40-200 mg of a filler, 2-20 mg of a disintegrant which is sodium carboxymethyl starch, 0-6 mg of a binder which is hydroxypropyl cellulose, and 0.5-8 mg of a lubricant which is glyceryl behenate.

2. The pharmaceutical composition according to claim 1, wherein the pharmaceutical composition comprises: 8-20 mg of (E)-N-(3-cyano-7-ethoxy-4-(3-ethynylphenylamino)quinolin-6-yl)-4-(dimethylamino)but-2-enamide maleate or hydrate thereof, 50-200 mg of the filler, 4-20 mg of sodium carboxymethyl starch, 0.3-5 mg of hydroxypropyl cellulose, and 0.5-8 mg of glyceryl behenate.

3. The pharmaceutical composition according to claim 1, wherein the pharmaceutical composition comprises: 8-20 mg of (E)-N-(3-cyano-7-ethoxy-4-(3-ethynylphenylamino) quinolin-6-yl)-4-(dimethylamino)but-2-enamide maleate or hydrate thereof, 130-200 mg of the filler, 10-20 mg of sodium carboxymethyl starch, 1-3 mg of hydroxypropyl cellulose, and 1-8 mg of glyceryl behenate.

4. The pharmaceutical composition according to claim 1, wherein the filler is a sugar alcohol.

5. The pharmaceutical composition according to claim 4, wherein the sugar alcohol is selected from the group consisting of mannitol, xylitol, sorbitol, and lactose.

6. The pharmaceutical composition according to claim 5, wherein the sugar alcohol is mannitol.

7. The pharmaceutical composition according to claim 1, wherein the pharmaceutical composition comprises: 8-20 mg of (E)-N-(3-cyano-7-ethoxy-4-(3-ethynylphenylamino) quinolin-6-yl)-4-(dimethylamino)but-2-enamide maleate monohydrate.

8. The pharmaceutical composition according to claim 7, wherein a water content in the pharmaceutical composition is 5 wt % or less.

9. The pharmaceutical composition according to claim 8, wherein a water content in the pharmaceutical composition is 1.5 wt % or less.

10. The pharmaceutical composition according to claim 7, further comprising an impurity compound represented by Formula (II):

Formula (II)

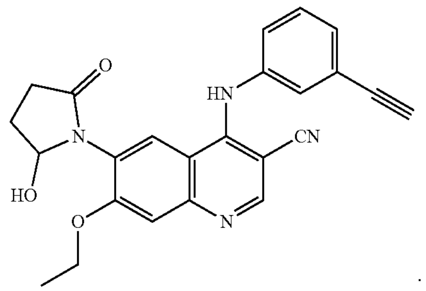

11. The pharmaceutical composition according to claim 10, wherein when exposed to 75% relative humidity at 40°° C. for 3 months, the pharmaceutical composition comprises the impurity compound represented by Formula (II) at no more than 0.47% as measured by High Performance Liquid Chromatography (HPLC).

12. The pharmaceutical composition according to claim 10, wherein when exposed to 75% relative humidity at 40° C. for 3 months, the pharmaceutical composition comprises the impurity compound represented by Formula (II) at no more than 0.22% as measured by HPLC.

13. The pharmaceutical composition according to claim 7, wherein the filler is selected from the group consisting of mannitol, xylitol, sorbitol, and lactose.

14. The pharmaceutical composition according to claim 13, wherein the filler is mannitol.

15. The pharmaceutical composition according to claim 7, wherein the pharmaceutical composition comprises: 8-20 mg of (E)-N-(3-cyano-7-ethoxy-4-(3-ethynylphenylamino) quinolin-6-yl)-4-(dimethylamino)but-2-enamide maleate monohydrate, 130-200 mg of mannitol, 10-20 mg of sodium carboxymethyl starch, 1-3 mg of hydroxypropyl cellulose, 1-8 mg of glyceryl behenate, and an impurity compound represented by Formula (II):

Formula (II)

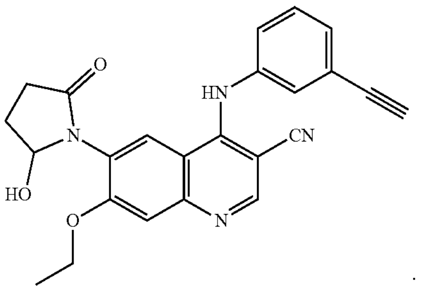

16. A pharmaceutical composition comprising: about 8.4 wt % to 11.6 wt % of (E)-N-(3-cyano-7-ethoxy-4-(3-ethynylphenylamino) quinolin-6-yl)-4-(dimethylamino) but-2-enamide maleate or hydrate thereof, about 75.6 wt % to 84 wt % of a filler that is mannitol or lactose, from 4.2 wt % to 11.6 wt % of sodium carboxymethyl starch, about 0.5 wt % to 1.3 wt % of hydroxypropyl cellulose, and from 0.6 wt % to 4.0 wt % of glyceryl behenate.

17. The pharmaceutical composition of claim 16, wherein the pharmaceutical composition comprises: about 8.4 wt % to 11.6 wt % of (E)-N-(3-cyano-7-ethoxy-4-(3-ethynylphenylamino)quinolin-6-yl)-4-(dimethylamino)but-2-enamide maleate monohydrate.

18. The pharmaceutical composition according to claim 16, further comprising an impurity compound represented by Formula (II):

Formula (II)

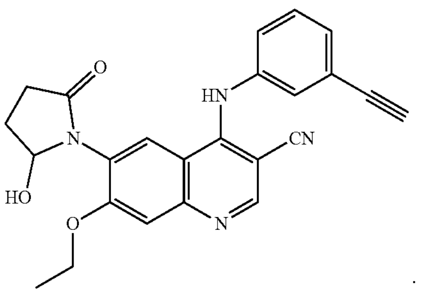

* * * * *